United States Patent [19]

Podder et al.

[11] Patent Number: 4,665,232

[45] Date of Patent: May 12, 1987

[54] PROCESS FOR THE PREPARATION OF 4-NITRODIPHENYLAMINES

[75] Inventors: Chiraranjan Podder, Dormagen; Harro Schlesmann, Odenthal, both of Fed. Rep. of Germany

[73] Assignee: Bayer Aktiengesellschaft, Leverkusen, Fed. Rep. of Germany

[21] Appl. No.: 817,502

[22] Filed: Jan. 9, 1986

[30] Foreign Application Priority Data

Jan. 19, 1985 [DE] Fed. Rep. of Germany ....... 3501698

[51] Int. Cl.$^4$ ............................................. C07C 85/04
[52] U.S. Cl. .................................................. 564/406
[58] Field of Search ......................................... 564/406

[56] References Cited

U.S. PATENT DOCUMENTS

| | | | |
|---|---|---|---|
| 3,313,854 | 4/1967 | Levy | 564/406 |
| 3,435,074 | 3/1969 | Terao et al. | 564/406 |
| 4,042,627 | 8/1977 | Kalopissis et al. | 564/406 X |
| 4,122,118 | 10/1978 | George et al. | 564/406 |
| 4,209,463 | 6/1980 | Maender et al. | 564/406 |
| 4,404,400 | 9/1983 | Heise et al. | 564/406 |
| 4,614,817 | 9/1986 | Maender et al. | 564/406 |

*Primary Examiner*—Paul F. Shaver
*Attorney, Agent, or Firm*—Connolly & Hutz

[57] ABSTRACT

The reaction of 4-nitrohalobenzenes with primary aromatic amines in the presence of potassium carbonate and copper compounds to produce 4-nitrodiphenylamine results in products with improved purity and yield if (1) carbonic acid amides or their derivatives are added, (2) 3 to 5 mol of amine are used per mole of halonitrobenzene and (3) 1.2 to 2 mol of the amine are added before the beginning of the reaction and the remainder during the reaction at such a rate that the molar excessive amine over halonitrobenzene is always from 100 to 400%.

4 Claims, No Drawings

PROCESS FOR THE PREPARATION OF 4-NITRODIPHENYLAMINES

This invention relates to a process for the preparation of 4-nitrodiphenylamines by the reaction of 4-nitrohalobenzenes with primary aromatic amines in the presence of potassium carbonate and copper compounds.

The reaction of halonitrobenzenes with aromatic amines has been known for a long time. According to DE-PS No. 185 663, the reaction may be carried out in the presence of alkali metal carbonates and copper compounds as catalysts.

It is also known that this extremely slow reaction can be accelerated by using potassium carbonate and removing the water of reaction by azeotropic distillation. According to Example 1 of U.S. Pat. No. 2,927,943, moderately pure 4-nitrodiphenylamine was obtained in 73% of the theoretical yield under these conditions after a reaction time of 21 hours. It is also known from U.S. Pat. No. 4,155,936 that the reaction of halonitrobenzene with primary aromatic amines not only has the disadvantage of long reaction times but is accompanied by contamination of the nitrodiphenylamines due to the formation of considerable quantities of tars and by-products and by the formation of nitrobenzene due to reductive dehalogenation (see U.S. Pat. No. 3,313,854, column 3, lines 64, 65).

It has already been proposed to add cocatalysts, solubilizing agents and dipolar aprotic solvents to the reaction mixture to overcome these disadvantages.

Formanilide according to U.S. Pat. No. 3,313,854, acetanilide according to DE-AS No. 1 518 307, salicylic anilide according to DE-AS No. 1 117 594 and ε-caprolactam according to JP No. 8 122 751, however, have only a slight effect.

The proposals made in U.S. Pat. No. 3,121,736 (addition of aminocarboxylic acids, of alkyldiaminopolycarboxylic acids and salts, of disalicylal-diaminoalkanes, of o-hydroxybenzalaminophenols, of polyphosphates, of carboxymethylmercaptosuccinic acid or of Schiff's bases of salicylaldehydes), in JP-OS No. 8 240 445 (addition of benzyl trimethylammonium bromide, benzyltributylphosphonium chloride, benzyltriphenylphosphonium chloride, tetraethylammonium chloride or tetrabutylphosphonium chloride) or in DE-OS No. 3 137 041 (addition of imidazol(in)e, pyrimidine, bicyclic amidine, triazine, phenanthroline, dipyridine or bis-quinoline) give rise to problems in working up the product.

Although the use of caesium compounds according to DE-OS No. 3 246 151 provides improvements in yields, the high cost of these compounds considerably increases the cost of the process.

The addition of polyethers of differing structures described in U.S. Pat. No. 4,155,936, JP-OS No. 80 100 342 and JP-OS No. 82 02 243 also fails to provide any improvement.

Other additives which, however, also fail to provide any improvement, have been described in U.S. Pat. No. 3,055,940 (dimethylformamide and hexamethylphosphoric acid triamide), U.S. Pat. No. 3,277,175 (dimethylsulphoxide), DE-OS No. 2 633 811 (N-methylpyrrolidone) and JP-OS No. 71/09452 (diethylformamide).

A process has now been found for the preparation of 4-nitrodiphenylamines corresponding to formula (I)

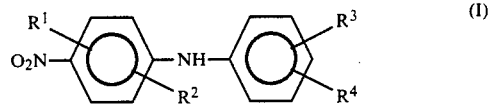

wherein
$R^1$, $R^2$, $R^3$ and $R^4$ are identical or different and stand for hydrogen or an alkyl group with 1 to 9 carbon atoms,
by the reaction of halonitrobenzenes corresponding to formula (II)

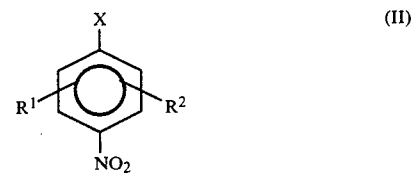

wherein
X stands for chlorine or bromine and
$R^1$ and $R^2$ have the meaning indicated above,
with primary amines corresponding to formula (III)

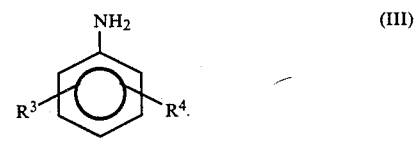

wherein
$R^3$ and $R^4$ have the meaning indicated above, in the presence of potassium carbonate and copper compounds, characterised in that (1) carbonic acid amides or derivatives thereof are added, (2) 3 to 5 mol of amine are used per mol of halonitrobenzene and (3) from 1.2 to 2 mol of amine is added before the beginning of the reaction and the remainder is added during the reaction at such a rate that the molar excess of amine over halonitrobenzene is constantly from 100 to 400%.

The alkyl groups $R^1$ to $R^4$ preferably have 1 to 3 carbon atoms.

Suitable halonitrobenzenes are, for example, 4-nitrochlorobenzene, 4-nitrobromobenzene, 4-nitro-2-methyl-chlorobenzene and 4-nitro-3-methyl-chlorobenzene.

Examples of suitable primary aromatic amines include aniline, o-toluidine, m-toluidine, p-toluidine, 4-ethylaniline, 4-butylaniline, 4-isopropylaniline, 3,5-dimethylaniline and 2,4-dimethylaniline.

The aromatic amines may, of course, also be used in the form of mixtures, in particular isomeric mixtures. They are generally used in quantities of about 1 to 6 mol, preferably 1.5 to 4.5 mol, especially 1.7 to 2.5 mol per mol, of halonitrobenzene.

The process is preferably used for the preparation of 4-nitrodiphenylamine from 4-nitrochlorobenzene and aniline.

The following are examples of copper catalysts which may be used in the process according to the invention: Copper-(I)-iodide, copper-(I)-chloride, copper-(II)-chloride, copper-(I)-bromide, copper-(II)-bromide, copper-(I)-cyanide, copper-(I)-oxide, copper-(II)-oxide, copper-(II)-carbonate, basic copper-(II)-carbonate, copper-(II)-sulphate, copper-(II)-nitrate, copper- (II)-formate, copper-(II)-acetate and organic and inorganic coordination compounds of monovalent or divalent copper. It is preferred to use copper compounds containing oxygen, such as copper-(II)-oxide, copper-(II)-carbonate, basic copper-(II)-carbonate or copper-(I)-oxide, the copper catalysts being used in a quantity of from 0.001 to 0.1 mol, preferably from 0.01 to 0.05 mol per mol of halonitrobenzene put into the process. The copper catalysts may be used either singly or as mixtures.

The carbonic acid amides and their derivatives used may be urethanes, ureas, ureides, semi-carbazides, guanidines or polymers or esters of isocyanic acid, in particular urethane, N-ethylurethane, urea, N-ethylurea, N-phenylurea, hydrazodicarbonamide, biuret, N-phenylguanidine, N,N'-diphenyl-guanidine, cyamelide and phenylisocyanate.

The carbonic acid amides and their derivatives are used in a quantity of from 0.01 to 0.1 mol, preferably from 0.025 to 0.05 mol per mol of halonitrobenzene.

Rubidium and caesium compounds may in addition be added in catalytic quantities to the reaction mixture.

Potassium carbonate may be used in the equivalent quantity or in excess, up to 1.5 times the equivalent quantity.

The water of the reaction is advantageously removed from the reaction mixture by distillation with the aid of a carrier.

The carriers used may be, for example, xylene, toluene, benzene, chlorobenzene or chlorotoluene.

If necessary for adjusting or maintaining the reaction temperature range, the process according to the invention may be carried out in the presence of additional diluents, e.g. inert hydrocarbons such as xylene. The aromatic primary amines may themselves be used for this purpose.

The reaction temperatures of the process according to the invention may vary within wide limits and are generally from 140° to 225° C., preferably from 180° to 210° C.

The process according to the invention may be carried out by the usual methods, either continuously or batchwise.

Working up of the reaction mixture may also be carried out by various methods. The salts present in the reaction mixture may be removed physically at elevated temperatures by centrifuging or filtration. After washing with warm xylene and drying, a light grey, pulverulent solid is left behind.

Xylene, unreacted halonitrobenzene, primary aromatic amine and solvents can be completely removed from the filtrate in a rotary evaporator or coil evaporator under a vacuum of 5 to 50 mbar and at a temperature of 150° to 220° C., the nitrodiphenylamines being obtained in the form of a melt which solidifies on cooling. The mixture obtained as distillate may be used in the next reaction mixture without further treatment. Alternatively, the filtrate may be partly distilled under vacuum and the nitrodiphenylamines substantially separated by crystallisation. The nitrodiphenylamines are then obtained in a highly pure form which can be used directly for further processing. The distillate from the vacuum distillation and the mother liquor from crystallisation may be used again.

According to another variation, water is added to the reaction mixture, the potassium salts are dissolved and copper oxide is separated by filtration. Xylene, unreacted p-nitrochlorobenzene and primary amine may be removed from the filtrate by steam distillation. Nitrodiphenylamine is then obtained in the form of a granulate which may be used for further processing. The copper catalyst and the cocatalyst may be used repeatedly. If necessary, their full activity may be maintained by adding fresh catalyst or cocatalyst in a smaller quantity than the originally added.

4-Nitrodiphenylamines may be prepared in high yields and with a high degree of purity within short reaction times by the process according to the invention. The formation of by-products occurs only to a slight extent in the process according to the invention.

The 4-nitrodiphenylamines prepared by the process according to the invention may readily be reduced to aminodiphenylamines by known methods and as such are valuable intermediate products for the manufacture, for example, of dyes or stabilizers for rubber (see U.S. Pat. No. 3,163,616).

EXAMPLE 1

157.6 g of p-nitrochlorobenzene, 186 g of aniline, 100 g of potassium carbonate, 20 ml of xylene, 2 g of copper oxide and 2.23 g of urethane were introduced into a 1-liter flask equipped with stirrer and distillation attachment with water separator.

The reaction mixture was heated to 195° C. with stirring. A further 186 g of aniline were then added portionwise and the contents of the flask were maintained at a temperature of 195° C. until 10.5 to 11 ml of water had been separated, and the 4-chloro-nitrobenzene content was determined by liquid chromatography on a sample. If the 4-chloro-nitrobenzene content was found to be less than 1.5% of the original quantity, the reaction was stopped by cooling; otherwise, the reaction was continued until this value was reached. The total reaction time was 8 hours.

250 ml of water were added to the reaction mixture which was then filtered at 90° C. and the volatile constituents were driven off with steam. The aqueous phase of the contents of the flask was separated off and the organic phase solidified on cooling. 212.8 g of a yellow, granular substance was obtained. According to liquid chromatographic analysis, this substance contained 91.5% by weight of 4-nitrodiphenylamine, corresponding to a 90.9% yield, based on 4-nitrochlorobenzene.

Further experiments yielded the following results:

| Example | Additive | Quantity added (g) | Reaction time (h) | 4-nitrodiphenylamine content (% by weight) | Yield of crude 4-nitro diphenylamine (g) | Yield (% of theoretical) |
|---|---|---|---|---|---|---|
| 2 | Urea | 1.50 | 8 | 91.1 | 211.3 | 89.9 |
| 3 | N—ethylurea | 2.20 | 7 | 90.4 | 212.1 | 89.5 |
| 4 | Biuret | 2.85 | 10.5 | 89.6 | 210.5 | 88.1 |
| 5 | Hydrazodicarbonamide | 2.95 | 10.0 | 91.0 | 206.6 | 87.8 |
| 6 | N,N'—diphenylguanidine | 5.00 | 10.5 | 87.9 | 214.4 | 88.0 |

| Example | Additive | Quantity added (g) | Reaction time (h) | 4-nitrodiphenyl-amine content (% by weight) | Yield of crude 4-nitro diphenyl-amine (g) | Yield (% of theoretical) |
|---|---|---|---|---|---|---|
| 7 | Cyamelide | 2.50 | 12.0 | 90.9 | 210.2 | 89.2 |
| 8 | Phenylisocyanate | 2.98 | 12.0 | 89.1 | 212.7 | 88.5 |

What is claimed is:

1. Process for the preparation of 4-nitrodiphenylamine corresponding to the formula

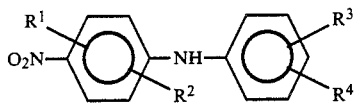

wherein
R¹, R², R³ and R⁴, which may be identical or different, stand for hydrogen or an alkyl group having 1 to 9 carbon atoms
by the reaction of halonitro compounds corresponding to the formula

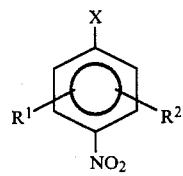

wherein
X stands for chlorine or bromine and
R¹ and R² have the meanings indicated above with primary aromatic amines corresponding to the formula

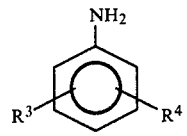

wherein
R³ and R⁴ have the meanings indicated above in the presence of potassium carbonate and copper compounds, characterised in that (1) carbonic acid amides or derivatives thereof are added, (2) 3 to 5 mol of amine are added per mol of halonitrobenzene and (3) from 1.2 to 2 mol of the amine are added before the beginning of the reaction at such a rate that the molar excess of amine over halonitrobenzene is constantly from 100 to 400%.

2. Process according to claim 1, characterised in that R₁, R₂, R₃ and R₄ denote hydrogen.

3. Process according to claim 1, characterised in that from 0.01 to 0.1 mol of carbonic acid amide or a derivative thereof is used per mol of halonitrobenzene.

4. Process according to claim 1, characterised in that urethane, N-ethylurethane, urea, N-ethylurea, N-phenylurea, hydrazodicarbonamide, biuret, N-phenylguanidine, N,N'-diphenylguanidine, cyamelide or phenylisocyanate is used.

* * * * *